(12) United States Patent
Weeratunga et al.

(10) Patent No.: US 8,101,646 B2
(45) Date of Patent: Jan. 24, 2012

(54) AMORPHOUS FORM OF AN L-ARGININE SALT OF PERINDOPRIL AND PROCESSES FOR PREPARATION THEREOF

(75) Inventors: Gamini Weeratunga, Brantford (CA); Carlos B. Zetina-Rocha, Brantford (CA)

(73) Assignee: Apotex Pharmachem Inc., Brantford (CA)

( * ) Notice: Subject to any disclaimer, the term of this patent is extended or adjusted under 35 U.S.C. 154(b) by 316 days.

(21) Appl. No.: 12/553,255

(22) Filed: Sep. 3, 2009

(65) Prior Publication Data

US 2010/0056802 A1    Mar. 4, 2010

Related U.S. Application Data

(60) Provisional application No. 61/093,782, filed on Sep. 3, 2008.

(51) Int. Cl.
*A61K 31/403* (2006.01)
*C07D 209/42* (2006.01)

(52) U.S. Cl. .................... 514/412; 548/452
(58) Field of Classification Search .................. None
See application file for complete search history.

(56) References Cited

U.S. PATENT DOCUMENTS

| 4,508,729 A | 4/1985 | Vincent et al. |
| 6,696,481 B2 | 2/2004 | Damien et al. |

FOREIGN PATENT DOCUMENTS

| WO | WO2007099216 A2 | 9/2007 |
| WO | WO2007099217 A2 | 9/2007 |
| WO | WO 2009157018 A2 * | 12/2009 |

* cited by examiner

*Primary Examiner* — Yong Chu
*Assistant Examiner* — Michael Barker

(57) ABSTRACT

In illustrative embodiments, there is provided an amorphous form of L-arginine salt of perindopril which may be particularly suitable for pharmaceutical applications, and processes for preparing said form.

32 Claims, 2 Drawing Sheets

AMORPHOUS FORM OF AN L-ARGININE SALT OF PERINDOPRIL AND PROCESSES FOR PREPARATION THEREOF

TECHNICAL FIELD

The present invention relates to an amorphous form of an L-arginine salt of perindopril of formula (1) and methods for its preparation.

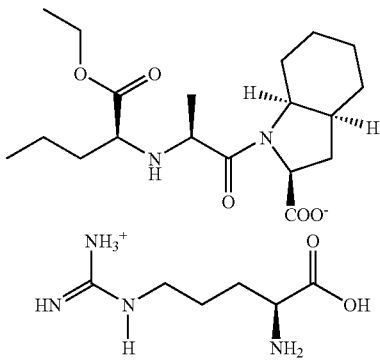

(1)

BACKGROUND

Perindopril, (2S,3aS,7aS)-1-[(2S)-2-[[(1S)-1-(ethoxycarbonyl)butyl]amino]-1-oxopropyl]octahydro-1H-indole-2-carboxylic acid, is a compound effective for the treatment of hypertension and heart failure and it is marketed the United States as its tert-butylamine (or erbumine) salt under the commercial name Aceon®.

Perindopril and its pharmaceutically acceptable salts have important therapeutic properties. Their mode of action is to reduce or completely eliminate the activity of certain enzymes which are responsible, in some cases, for hypertension or cardiac insufficiency. In particular, perindopril inhibits the angiotensin-converting enzyme (ACE) thereby preventing the transformation of angiotensin I to angiotensin II. The hormone angiotensin II causes blood vessels to constrict which results in high blood pressure.

Pharmaceutically acceptable salts of perindopril which exhibits both good bioavailability and adequate stability for long term storage of the corresponding pharmaceutical compositions have been difficult to find. In particular The non-salt form of perindopril, as well as many salt forms, are unsuitable for long term storage due to liquefaction or decomposition of the compound.

U.S. Pat. No. 4,508,729 describes substituted imino-diacids, and more particularly to substituted azabicycloalkanedicarboxylic acids, their preparation and pharmaceutical compositions which contain them.

U.S. Pat. No. 6,696,481 describes the arginine salt of perindopril, its hydrates and also the pharmaceutical compositions comprising it. Also described is the salt of natural arginine (L-arginine).

WO 2007/099216 concerns a beta-crystalline form of formula (I), characterized by its X-ray powder diffraction diagram:

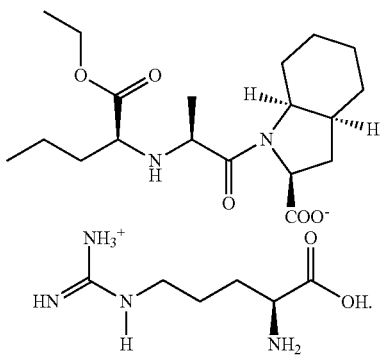

(1)

WO 2007/099217 relates to an alpha crystalline form of Formula (I), characterized by its X-ray powder diffraction diagram:

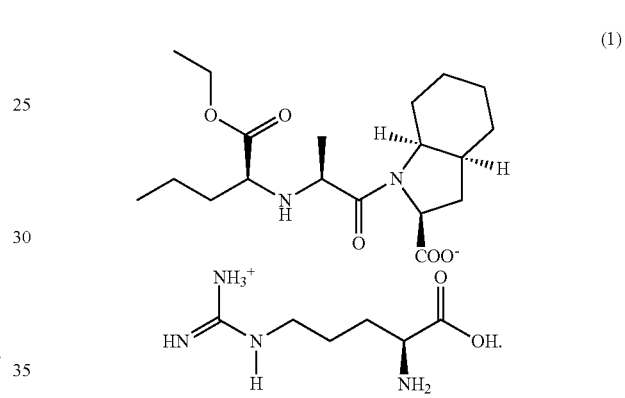

(1)

SUMMARY

This invention relates to an amorphous form of an L-arginine salt of perindopril. The amorphous form may be suited to pharmaceutical applications. The amorphous form may exhibit increased solubility and thermal stability relative to other salts of perindopril. This characteristic is often desirable for pharmaceutically active ingredients since increased solubility results in better oral bioavailability of the active ingredient and/or better dissolution for a liquid formulation of the pharmaceutically active ingredient.

Embodiments of this invention may provide several desirable characteristics. For example, the amorphous forms of the L-arginine salt of perindopril of the present invention may be free-flowing, easily filterable, and/or thermally stable. The amorphous forms of the L-arginine salt of perindopril of the present invention may be easily dried on a variety of scales, including, but not limited to, on an industrial scale. Some of these attributes may be attributed to level of residual solvents found in the amorphous forms of the L-arginine salt of perindopril of the present invention. The amorphous forms of the L-arginine salt of perindopril of the present invention may be more soluble relative to other known forms of perindopril arginine salt.

In illustrative embodiments of the present invention, there is provided a process for preparing the amorphous form of the L-arginine salt of perindopril comprising:
 a. combining L-arginine and perindopril in a suitable organic solvent or mixture of solvents;

b. heating the mixture and optionally filtering the mixture;
c. removing the solvent from the solution;
d. optional drying In illustrative embodiments of the present invention there is provided a process for the preparation or purification of the amorphous form of the L-arginine salt of perindopril comprising:
   a. forming a solution of the L-arginine salt of perindopril in a medium-polarity organic solvent;
   b. precipitating the amorphous salt by addition of a low-polarity organic solvent;
   c. filtering the mixture;
   d. optional drying In illustrative embodiments of the present invention, there is provided an amorphous form of an L-arginine salt of perindopril of formula 1:

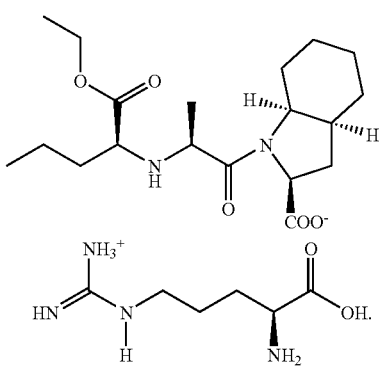

(1)

In illustrative embodiments of the present invention, there is provided an amorphous form of the L-arginine salt of perindopril described herein having a PXRD diffractogram comprising one or more broad diffuse halos.

In illustrative embodiments of the present invention, there is provided an amorphous form of the L-arginine salt of perindopril described herein having a PXRD diffractogram lacking a discernible peak.

In illustrative embodiments of the present invention, there is provided an amorphous form of the L-arginine salt of perindopril described herein having a PXRD diffractogram substantially similar to a PXRD diffractogram as depicted in FIG. 1

In illustrative embodiments of the present invention, there is provided an amorphous form of the L-arginine salt of perindopril described herein having an IR spectrum substantially similar to an IR spectrum as depicted in FIG. 2

In illustrative embodiments of the present invention, there is provided an amorphous form of the L-arginine salt of perindopril described herein characterized by an IR spectrum (1% KBr) showing characteristic peaks expressed in cm−1 at approximately 2933, 1732, 1445, 1392,1 189, and 1024.

In illustrative embodiments of the present invention, there is provided a process for preparation of the amorphous form of the L-arginine salt of perindopril as described herein comprising: a) combining L-arginine and perindopril in a suitable organic solvent, thereby forming a mixture; b) heating the mixture thereby forming a second mixture; and c) removing the solvent from the second mixture thereby forming the amorphous form of the L-arginine salt of perindopril.

In illustrative embodiments of the present invention, there is provided a process described herein further comprising filtering the second mixture prior to removing the solvent from the second mixture.

In illustrative embodiments of the present invention, there is provided a process described herein further comprising drying the amorphous form of the L-arginine salt of perindopril.

In illustrative embodiments of the present invention, there is provided a process described herein wherein the suitable organic solvent is a mixture of suitable organic solvents.

In illustrative embodiments of the present invention, there is provided a process described herein wherein the suitable organic solvent comprises a $C_1$ to $C_3$ chlorinated hydrocarbon.

In illustrative embodiments of the present invention, there is provided a process described herein wherein the suitable organic solvent comprises a $C_1$ to $C_4$ aliphatic alcohol.

In illustrative embodiments of the present invention, there is provided a process described herein wherein the suitable organic solvent comprises methylene chloride.

In illustrative embodiments of the present invention, there is provided a process described herein wherein the suitable organic solvent is ethanol or methanol.

In illustrative embodiments of the present invention, there is provided a process described herein wherein the temperature is from about 50° C. to about 100° C.

In illustrative embodiments of the present invention, there is provided a process described herein wherein the temperature about 78° C.

In illustrative embodiments of the present invention, there is provided a process described herein wherein the suitable organic solvent is removed by distillation.

In illustrative embodiments of the present invention, there is provided a process described herein wherein the suitable organic solvent is removed by distillation under reduced pressure.

In illustrative embodiments of the present invention, there is provided a process described herein wherein the suitable organic solvent is removed by spray-drying.

In illustrative embodiments of the present invention, there is provided a process described herein wherein the suitable organic solvent is removed by evaporation.

In illustrative embodiments of the present invention, there is provided a process for preparation of the amorphous form of the L-arginine salt of perindopril as described herein comprising: a) forming a solution of the L-arginine salt of perindopril in at least one medium-polarity organic solvent; b) precipitating the amorphous form of the L-arginine salt of perindopril by addition of at least one low-polarity organic solvent thereby forming a mixture; and c) filtering the mixture.

In illustrative embodiments of the present invention, there is provided a process described herein wherein the forming of the solution of the L-arginine salt of perindopril in at least one medium polarity organic solvent comprises mixing the at least one medium-polarity organic solvent with an L-arginine salt of perindopril having a purity less than the purity of the amorphous form of the L-arginine salt of perindopril obtained after filtering the mixture.

In illustrative embodiments of the present invention, there is provided a process described herein further comprising drying a solid obtained from filtering the mixture.

In illustrative embodiments of the present invention, there is provided a process described herein wherein the at least one medium-polarity organic solvent is selected from at least one of the group consisting of: a $C_1$ to $C_3$ chlorinated hydrocarbon.

In illustrative embodiments of the present invention, there is provided a process described herein wherein the at least one medium-polarity organic solvent is selected from at least one of the group consisting of: a $C_3$ to $C_{10}$ aliphatic ester.

In illustrative embodiments of the present invention, there is provided a process described herein wherein the at least one medium-polarity organic solvent comprises methylene chloride.

In illustrative embodiments of the present invention, there is provided a process described herein wherein the at least one low-polarity organic solvent comprises at least one of the group consisting of: a $C_5$ to $C_{12}$ substituted aliphatic hydrocarbon and a $C_5$ to $C_{12}$ unsubstituted aliphatic hydrocarbon.

In illustrative embodiments of the present invention, there is provided a process described herein wherein the at least one low-polarity organic solvent comprises at least one of the group consisting of: heptanes and hexanes.

DETAILED DESCRIPTION

Figure 1:
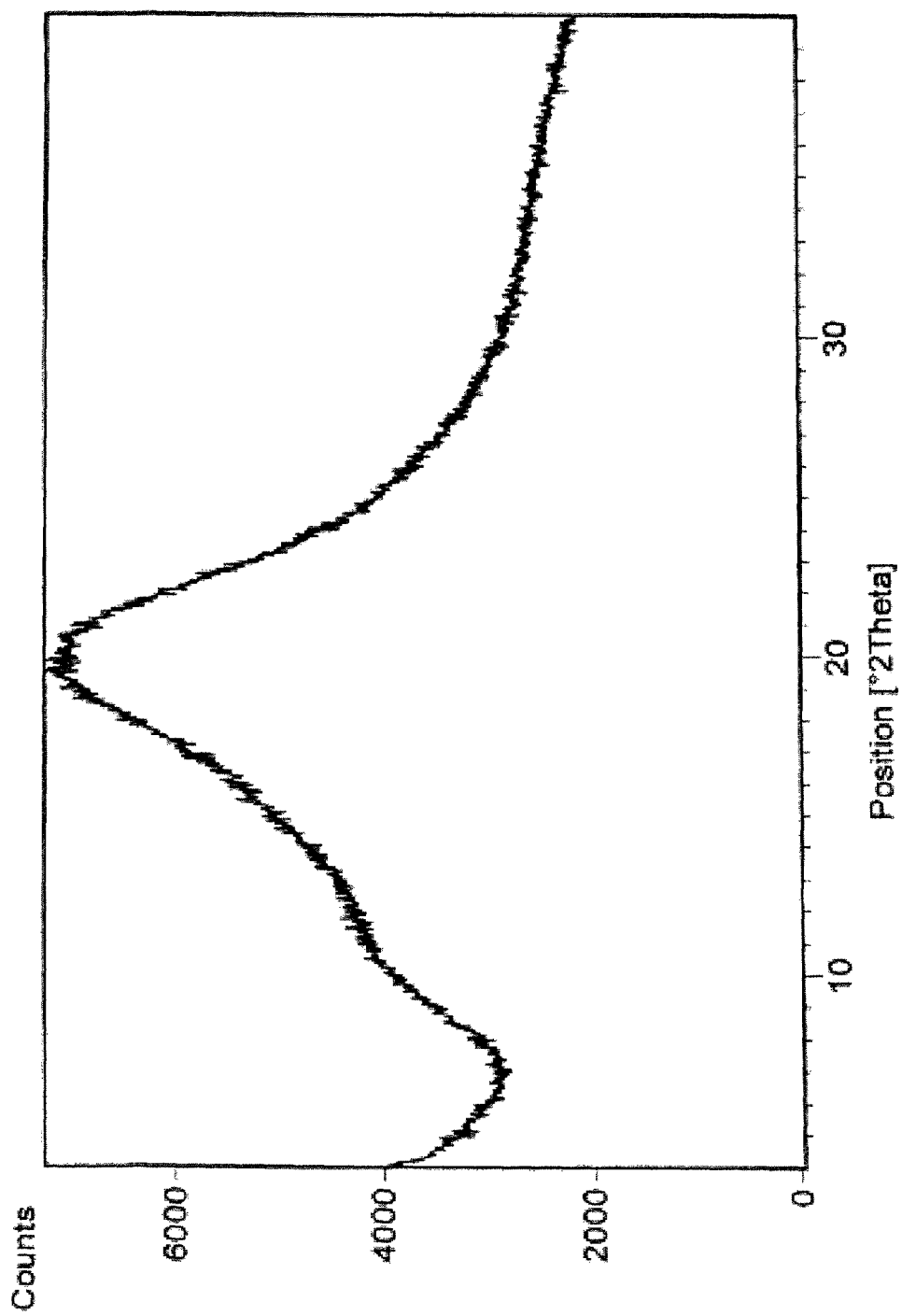
FIG. 1 is a Powder X-ray Diffraction (PXRD) pattern of the amorphous form of L-arginine salt of Perindopril (CuKα)

In one embodiment, the present invention comprises amorphous L-arginine salt of perindopril characterized by a halo-PXRD pattern as shown in FIG. 1.

The amorphous nature of the L-arginine salt of perindopril produced by this process is demonstrated by the halo-PXRD pattern which is indicative of the lack of a defined crystal structure.

In another embodiment, the present invention comprises amorphous L-arginine salt of perindopril characterized by an IR spectrum (1% KBr) showing characteristic peaks expressed in $cm^{-1}$ at approximately 2933, 1732, 1445, 1392, 1189, and 1024.

Figure 2:
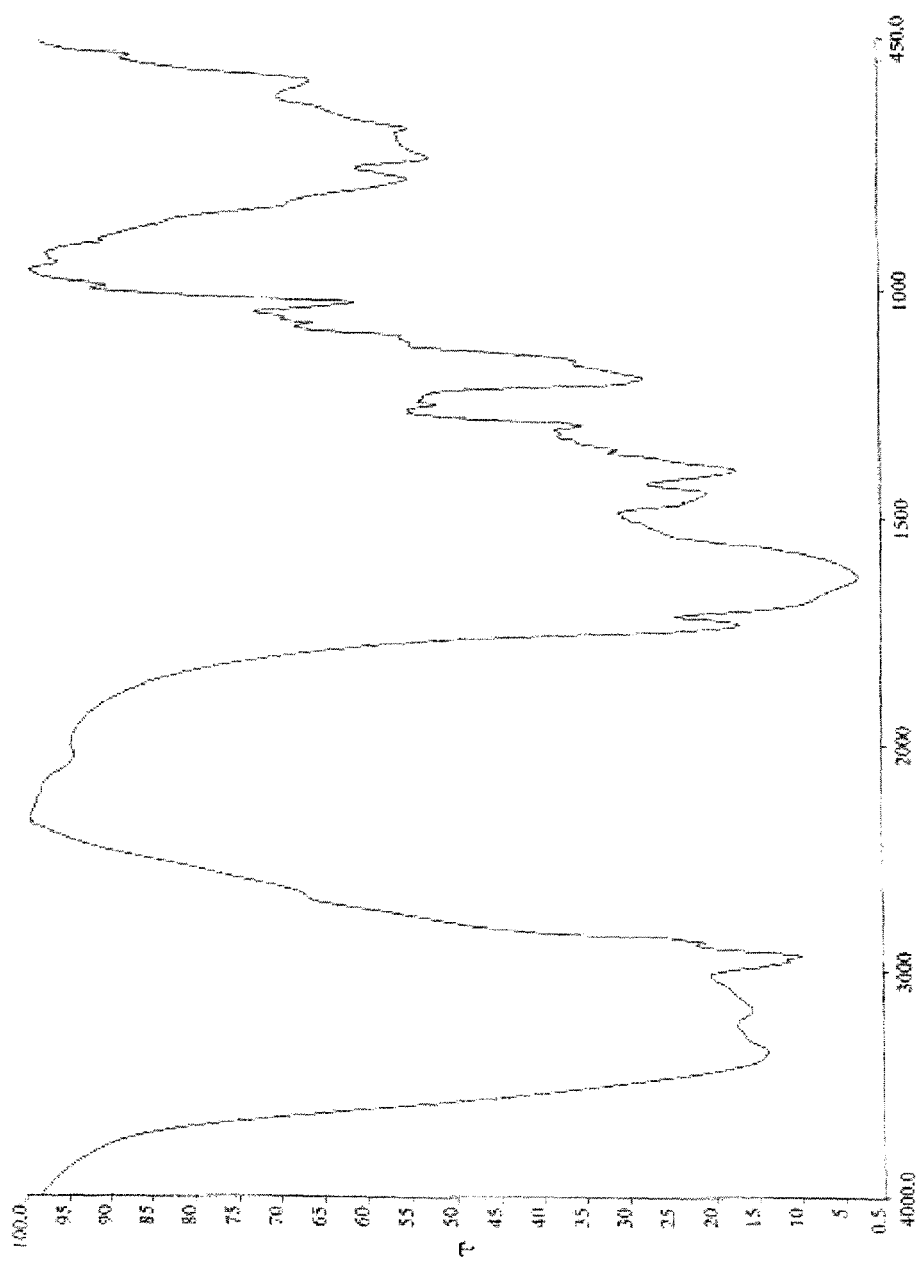
FIG. 2 is an Infrared (IR) spectrum of the amorphous form of L-arginine salt of Perindopril (1% KBr)

In another embodiment, the present invention comprises amorphous L-arginine salt of perindopril characterized by an IR spectrum (1% KBr) substantially as shown in FIG. 2.

In one embodiment of the present invention, the amorphous form of the L-arginine salt of perindopril is prepared by a process comprising:
 a. combining L-arginine and perindopril in a suitable organic solvent or mixture of solvents;
 b. heating the mixture and optionally filtering the mixture;
 c. removing the solvent from the solution;
 d. optional drying In one embodiment of the present invention, the solvent may be removed by distillation, distillation at reduced pressure, evaporation and/or spray drying. A suitable organic solvent may be selected from the group consisting of $C_1$ to $C_3$ chlorinated hydrocarbons such as methylene chloride; and $C_1$ to $C_4$ alcohols such as methanol and ethanol; and mixtures thereof. The mixture may be heated to a temperature between about 20° C. and about 100° C., and optionally filtered prior to solvent removal. The stoichiometric ratio of perindopril to L-arginine is about 1:1.

In one embodiment of the present invention, to a solution of perindopril in methylene chloride, typically about 2 to 4 volumes at about 15° C. to about 30° C., more preferably about 2 volumes at about 25° C. is added ethanol, preferably about 3 to 8 volumes, and more preferably about 5 volumes. This mixture is concentrated under vacuum to about 2 volumes, followed by addition of about 3 to 12 volumes of ethanol, more preferably about 10 volumes and about 1 mole equivalent of L-arginine. The mixture is then heated at about 20° C. to about 100° C., more preferably from about 30° C to about 78° C., most preferably from about 50° C. to about 78° C. The mixture is then optionally filtered and the filtrate cooled to about 20° C. to about 40° C., more preferably to about 20° C. to about 30° C., and then concentrated under vacuum to dryness.

In a further embodiment, the present invention encompasses a process for the preparation and/or purification of the amorphous form of the L-arginine salt of perindopril comprising:
 a. forming a solution of the L-arginine salt of perindopril in a medium-polarity organic solvent;
 b. precipitating the amorphous salt by addition of a low-polarity organic solvent;
 c. filtering the mixture;
 d. optional drying In one embodiment of the present invention the L-arginine salt of perindopril is combined with about 2 volumes to about 12 volumes, more preferably about 3 volumes to about 6 volumes of a medium-polarity organic solvent to form a mixture. The medium-polarity organic solvent may be selected from the group consisting of $C_1$ to $C_3$ chlorinated hydrocarbons such as methylene chloride; $C_3$ to $C_{10}$ aliphatic esters such as ethyl acetate, and mixtures thereof. This mixture is heated to a temperature between about 25° C. to about 100° C., more preferably from about 40° C. to about 80° C., in order to dissolve the L-arginine salt of perindopril. This solution may be optionally filtered, if desired, and then re-heated from about 40° C. to about 80° C. About 8 to about 20 volumes of a low-polarity organic solvent are then added and the mixture is cooled to a temperature between about 40° C. to about −5° C., more preferably to a temperature between about 20° C. to about 0° C. The low-polarity organic solvent may be selected from $C_5$ to $C_{12}$ substituted and unsubstituted aliphatic hydrocarbons, such as hexanes or heptanes. The material is then isolated by filtration.

The following examples are merely representative of the present invention and are not intended to be limiting.

Example 1

Preparation of Amorphous L-Arginine Salt of Perindopril from Perindopril

To a solution of perindopril (83.4 g) in methylene chloride (200 mL) was added anhydrous ethanol (500 mL) and the mixture was concentrated under vacuum to a volume of 200 mL. Ethanol (800 mL) was added to the mixture and then this was concentrated under vacuum to a volume of 800 mL. L-Arginine (39.4 g) was added, followed by ethanol (800 mL) and the mixture was heated to 70-75° C. whereupon more ethanol (200 mL) was added and the mixture stirred at 70-75° C. for about 1 h. The mixture was cooled to 45-50° C. and stirred for about 1 h. The mixture was then cooled to 20-25° C., filtered and the filtrate was concentrated to dryness under vacuum. The white solid obtained was dried in vacuo. This provided 116.5 grams of amorphous L-arginine salt of perindopril having the same PXRD and IR as shown in FIGS. 1 and 2, respectively.

Example 2

Preparation and Purification of Amorphous L-Arginine Salt of Perindopril by Precipitation The L-Arginine salt of perindopril (115 g, HPLC purity of 98.1%) was suspended in ethyl acetate (460 mL) and heated to reflux (77° C.). The mixture was filtered hot and washed with hot ethyl acetate (115 mL). The filtrate was again heated to reflux (77° C.) and heptanes (2020 mL) was added. The mixture was cooled to 20-25° C. and stirred for another 15 hours, filtered, and washed with a mixture of ethyl acetate (178 mL) and heptanes (52 ml). The damp solid was dried in vacuo to yield amorphous L-arginine salt of perindopril (87.5 g) with a HPLC purity of 99.8% and having the same analytical characteristics as shown in FIGS. 1 and 2.

While the foregoing provides a detailed description of a preferred embodiment of the invention, it is to be understood that this description is illustrative only of the principles of the invention and not limitative. Furthermore, as many changes can be made to the invention without departing from the scope of the invention, it is intended that all material contained herein be interpreted as illustrative of the invention and not in a limiting sense.

The invention claimed is:

1. An amorphous form of an L-arginine salt of perindopril of formula 1:

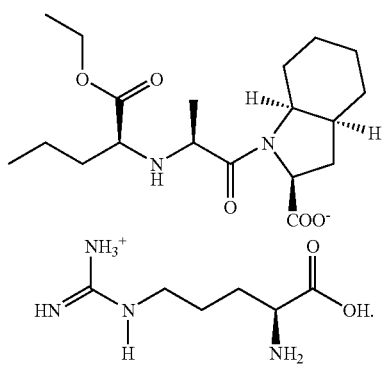

(1)

2. The amorphous form of the L-arginine salt of perindopril of claim 1 having a PXRD diffractogram comprising one or more broad diffuse halos.

3. The amorphous form of the L-arginine salt of perindopril of claim 1 having a PXRD diffractogram lacking a discernible peak.

4. The amorphous form of the L-arginine salt of perindopril of claim 1, having a PXRD diffractogram substantially similar to a PXRD diffractogram as depicted in FIG. 1.

5. The amorphous form of the L-arginine salt of perindopril of claim 1 having an IR spectrum substantially similar to an IR spectrum as depicted in FIG. 2.

6. The amorphous form of the L-arginine salt of perindopril of claim 1 characterized by an IR spectrum (1% KBr) showing characteristic peaks expressed in $cm^{-1}$ at approximately 2933, 1732, 1445, 1392, 1189, and 1024.

7. The amorphous form of an L-arginine salt of perindopril of claim 1 having a PXRD diffractogram comprising one or more broad diffuse halos and lacking a discernible peak and characterized by an IR spectrum (1% KBr) showing characteristic peaks expressed in $cm^{-1}$ at approximately 2933, 1732, 1445, 1392, 1189, and 1024.

8. A process for preparation of the amorphous form of the L-arginine salt of perindopril as claimed in claim 1 comprising:
   a) combining L-arginine and perindopril in a suitable organic solvent, thereby forming a mixture;
   b) heating the mixture thereby forming a second mixture; and
   c) removing the solvent from the second mixture thereby forming the amorphous form of the L-arginine salt of perindopril.

9. The process of claim 8 further comprising filtering the second mixture prior to removing the solvent from the second mixture.

10. The process of claim 8 further comprising drying the amorphous form of the L-arginine salt of perindopril.

11. The process of claim 8 wherein the suitable organic solvent is a mixture of suitable organic solvents.

12. The process of claim 8 wherein the suitable organic solvent comprises a $C_1$ to $C_3$ chlorinated hydrocarbon.

13. The process of claim 8 wherein the suitable organic solvent comprises a $C_1$ to $C_4$ aliphatic alcohol.

14. The process of claim 8 wherein the suitable organic solvent comprises methylene chloride.

15. The process of claim 8 wherein the suitable organic solvent is ethanol or methanol.

16. The process of claim 8 wherein the temperature is from about 50° C. to about 100° C.

17. The process of claim 8 wherein the temperature about 78° C.

18. The process of claim 8 wherein the suitable organic solvent is removed by distillation.

19. The process of claim 8 wherein the suitable organic solvent is removed by distillation under reduced pressure.

20. The process of claim 8 wherein the suitable organic solvent is removed by spray-drying.

21. The process of claim 8 wherein the suitable organic solvent is removed by evaporation.

22. The process for preparation of the amorphous form of the L-arginine salt of perindopril of claim 8 further comprising filtering the second mixture prior to removing the solvent from the second mixture; drying the amorphous form of the L-arginine salt of perindopril, wherein the suitable organic solvent is selected from the group consisting of: a $C_1$ to $C_3$ chlorinated hydrocarbon, a $C_1$ to $C_4$ aliphatic alcohol, methylene chloride, ethanol, methanol and mixtures thereof, wherein the temperature is from about 50° C. to about 100° C. and wherein the suitable organic solvent is removed by distillation, by distillation under reduced pressure, by spray-drying, or by evaporation.

23. The process of claim 22 wherein the temperature about 78° C.

24. A process for preparation of the amorphous form of the L-arginine salt of perindopril as claimed in claim 1 comprising:
   a) forming a solution of the L-arginine salt of perindopril in at least one medium-polarity organic solvent;
   b) precipitating the amorphous form of the L-arginine salt of perindopril by addition of at least one low-polarity organic solvent thereby forming a mixture; and
   c) filtering the mixture.

25. The process of claim 24 wherein the forming of the solution of the L-arginine salt of perindopril in at least one medium polarity organic solvent comprises mixing the at least one medium-polarity organic solvent with an L-arginine salt of perindopril having a purity less than the purity of the amorphous form of the L-arginine salt of perindopril obtained after filtering the mixture.

26. The process of claim 24 further comprising drying a solid obtained from filtering the mixture.

27. The process of claim 24 wherein the at least one medium-polarity organic solvent is selected from at least one of the group consisting of: a $C_1$ to $C_3$ chlorinated hydrocarbon.

28. The process of 24 wherein the at least one medium-polarity organic solvent is selected from at least one of the group consisting of: a $C_3$ to $C_{10}$ aliphatic ester.

29. The process of claim 24 wherein the at least one medium-polarity organic solvent comprises methylene chloride.

30. The process of claim 24 wherein the at least one low-polarity organic solvent comprises at least one of the group consisting of: a $C_5$ to $C_{12}$ substituted aliphatic hydrocarbon and a $C_5$ to $C_{12}$ unsubstituted aliphatic hydrocarbon.

31. The process of claim 24 wherein the at least one low-polarity organic solvent comprises at least one of the group consisting of: heptanes and hexanes.

32. The process for preparation of the amorphous form of the L-arginine salt of perindopril of claim 24 wherein the forming of the solution of the L-arginine salt of perindopril in at least one medium polarity organic solvent comprises mixing the at least one medium-polarity organic solvent with an L-arginine salt of perindopril having a purity less than the purity of the amorphous form of the L-arginine salt of perindopril obtained after filtering the mixture; and further comprising drying the L-arginine salt of perindopril obtained after filtering the mixture, wherein the at least one medium-polarity organic solvent is selected from at least one of the group consisting of: a $C_1$ to $C_3$ chlorinated hydrocarbon, a $C_3$ to $C_{10}$ aliphatic ester, methylene chloride and mixtures thereof and wherein the at least one low-polarity organic solvent comprises at least one of the group consisting of: a $C_5$ to $C_{12}$ substituted aliphatic hydrocarbon, a $C_5$ to $C_{12}$ unsubstituted aliphatic hydrocarbon, heptanes, hexanes and mixtures thereof.

\* \* \* \* \*